United States Patent
Collins

(10) Patent No.: US 9,206,388 B1
(45) Date of Patent: Dec. 8, 2015

(54) PROCESS FOR A SUSTAINABLE GROWTH OF ALGAE IN A BIOREACTOR AND FOR THE EXTRACTION OF A BIOFUEL PRODUCT

(71) Applicant: Ronny Collins, Durant, OK (US)

(72) Inventor: Ronny Collins, Durant, OK (US)

( * ) Notice: Subject to any disclaimer, the term of this patent is extended or adjusted under 35 U.S.C. 154(b) by 45 days.

(21) Appl. No.: 13/999,154

(22) Filed: Jan. 17, 2014

(51) Int. Cl.
*C12N 1/12* (2006.01)

(52) U.S. Cl.
CPC ......................................... *C12N 1/12* (2013.01)

(58) Field of Classification Search
None
See application file for complete search history.

(56) References Cited

U.S. PATENT DOCUMENTS

| | | | |
|---|---|---|---|
| 2,658,310 A | 11/1953 | Cook | |
| 5,951,875 A * | 9/1999 | Kanel et al. | 210/703 |
| 7,763,457 B2 | 7/2010 | Dunlop | |
| 8,033,047 B2 | 10/2011 | Rasmussen | |
| 2008/0096267 A1 | 4/2008 | Howard | |
| 2008/0102503 A1 | 5/2008 | Rush | |
| 2008/0293132 A1 | 11/2008 | Goldman | |
| 2008/0299643 A1 | 12/2008 | Howard | |
| 2009/0203116 A1 | 8/2009 | Bazaire | |
| 2009/0211150 A1 | 8/2009 | Wu | |
| 2010/0034050 A1 | 2/2010 | Erb | |
| 2010/0081835 A1 | 4/2010 | Wu | |
| 2010/0162621 A1 | 7/2010 | Seebo | |
| 2010/0227368 A1 | 9/2010 | Steiner | |
| 2010/0255458 A1 * | 10/2010 | Kinkaid | 435/3 |
| 2010/0297749 A1 * | 11/2010 | Aravanis et al. | 435/289.1 |
| 2012/0047797 A1 | 3/2012 | Berman | |
| 2012/0164722 A1 | 6/2012 | Wright | |
| 2012/0214198 A1 | 8/2012 | Trosch | |
| 2012/0252103 A1 * | 10/2012 | Deane | 435/257.1 |
| 2013/0061455 A1 | 3/2013 | Greene | |
| 2013/0092626 A1 * | 4/2013 | Zimmerman et al. | 210/601 |
| 2013/0280757 A1 | 10/2013 | Dvorak | |

OTHER PUBLICATIONS

Das, P., Lei, W., Aziz, S.S., and Obbard, J.P. "Enhanced algae growth in both phototrophic and mixotrophic culture under blue light", Bioresource Technology 2011, vol. 102, pp. 3883-3887.*

* cited by examiner

*Primary Examiner* — Renee Claytor
*Assistant Examiner* — Michelle F Paguio Frising
(74) *Attorney, Agent, or Firm* — Randal D. Homburg

(57) ABSTRACT

A process for accelerated and sustainable algae growth using a vertical tank photobioreactor, which includes steps involving the sustainable algae growth, preferably of the strain *nannochloropsis oculata*, the harvest of a portion of the algae in a harvester apparatus, the reduction and recycling of byproducts using recycled waste and conversion of gasses to useable and sustainable recycling within the process, the algae product supplied in wet or dry form for the further production of biofuels through the conversion of the algae to crude oil.

7 Claims, 1 Drawing Sheet

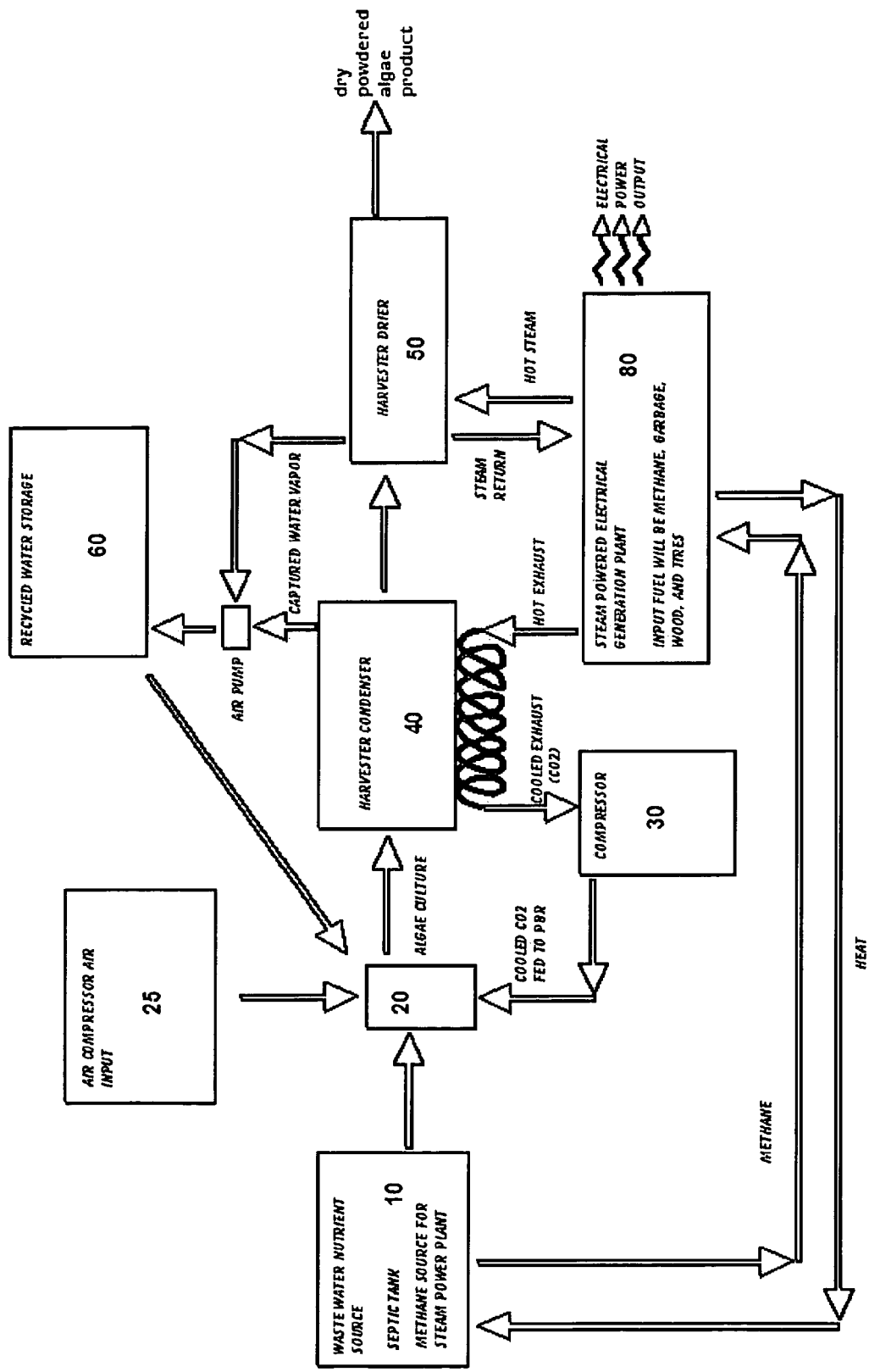

PROCESS FOR A SUSTAINABLE GROWTH OF ALGAE IN A BIOREACTOR AND FOR THE EXTRACTION OF A BIOFUEL PRODUCT

CROSS REFERENCE TO RELATED APPLICATIONS

None.

I. BACKGROUND OF THE INVENTION

1. Field of Invention

A process for accelerated and sustainable algae growth using a vertical tank photobioreactor, which includes steps involving the sustainable algae growth, preferably of the strain *nannochloropsis oculata*, the harvest of a portion of the algae in a harvester apparatus, the reduction and recycling of byproducts using recycled waste and conversion of gasses to useable and sustainable recycling within the process, the algae product supplied in wet or dry form for the further production of biofuels through the conversion of the algae to crude oil.

2. Description of Prior Art

A preliminary review of prior art patents was conducted by the applicant which reveal prior art patents in a similar field or having similar use. However, the prior art inventions do not disclose the same or similar elements as the present algae growth process, nor do they present the material components in a manner contemplated or anticipated in the prior art.

The present process involves the use of recycled waste water to provide a nutrient source for the algae bioreactor and for the production of methane used for production of steam for use in the later process, a photobioreactor, which incorporates internal LED light sources of an optimal wavelength to grow the algae source within the bioreactor, a compressed air source to supply the bioreactor with air to provide $CO_2$ to the algae culture within the bioreactor and also to move the biomass algae within the bioreactor at a gentle flow without damage to the algae, a harvester condenser for removal of excess water from the harvested algae from the bioreactor, a fresh water storage tank for recycling within the process as steam and reintroduction into the bioreactor, a harvester dryer for the completion of the water removal fro the wet algae harvest materials for the harvester condenser and a steam powered electrical generator to supply the system with electric power using the water taken from the primary harvester and harvester dryer, with garbage, trash, wood waster, rubbish and other combustible waster to supply heat to the process, to generate $CO_2$ for the growth of the algae with a byproduct from the process being dry powdered algae, fresh water, oxygen, fuel gas methane and electricity.

Prior art bioreactors include several products for the production of algae. In U.S. Patent Application No. 2010/0034050 to Erb, a bioreactor is disclosed using a plurality of turbine blades to stir the algae culture which has light in the turbine blades with air nozzles forming a sparger for the introduction of carbon dioxide. A bioreactor with an impeller is also shown in U.S. Patent Application NO. 2012/0047797 to Berman. A bioreactor for the growth of algae formed from a channel tube circulates water and algae with the tube containing a linear optic cable light to stimulate growth through the algae and water medium being circulated through the tubes in U.S. Patent Application No. 2009/0203116 to Bazaire. A similar flow bioreactor except using external light sources is shown in U.S. Patent Application No. 2013/0061455 to Greene and U.S. Pat. No. 7,763,457 to Dunlop. Light cones partial emerged in a tank containing algae along with nozzles to introduce gasses into the tank are shown in U.S. Pat. No. 8,033,047 to Rasmussen, the device using the gas injectors to stimulate a circular flow of the water and algae within the growth tank. A bioreactor having stationary vertical light rods, a gas diffuser plate, a lift wall separating the algae from a gas conduit and thermal tubes is disclosed in U.S. Patent Application NO. 2013/0280757 to Dvorak a light insert for a bioreactor is shown in U.S. Patent Application No. 2012/016722 to Wright, having legs suspending an LED light source upon a plate above the bottom of an algae tank, the LEDs being associated with the proper growth spectrum for the algae, although not fully disclosed in number or color.

Algae growth trays are shown in U.S. Patent Application No. 2010/0162621 to Seebo, having doors and panels over a plurality of stacked trays for the growth of algae cultures and uses horizontal lighting to stimulate the algae growth within a closed box containing the stacked trays. Outside light is used to illuminate a flowing stream of algae and water which is presented in glass columns in a very early U.S. Pat. No. 2,658,310 to Cook, for the cultivation of *Chlorella pyrenoidosa*, a type of algae.

Processes for the generation of algae for the production of oil are also disclosed in the prior art. Two patents to Howard, U.S. Patent Applications No. 2008/0299643 and 2008/0096267, involve processes where algae is cultivated in open pond systems covered on an acreage. Another process summarized in U.S. Patent Application No. 2008/0293132 to Goldman, uses focused light from a solar field focused within a photobioreactor (PBH) to generate algae and solar power. In a patent application to Rush, U.S. Patent Application No. 2008/0102503, cellulose, sugars, and fermentation combine with algae to create biodiesel and alcohol. In the Wu application, U.S. Patent Application NO. 2010/0081835, fish and algae are grown together and the algae is separated and cultured with a nutrient wherein lipids from the fish and algae extracts create a biofuel. A particular microalga *Chlorella protothecoides* is grown subsequent to inoculation to purify the specific type algae, two levels of carbohydrate feeding for the algae, harvesting the algae, drying the algae, extracting the oils from the algae and producing biodiesel by reaction of transesterification using the extracted oils as feedstock. It also uses a centrifuge in the drying process and an impeller throughout the growth process. In U.S. Patent Application NO. 2012/0214198 to Trosch, a treatment process is disclosed comprising the steps of an anaerobic biological treatment of an organic suspension, filtration of the suspension, supply of the filtered material derived from the suspension as a media component to an algal culture, burning methane generated in connection with the algae growth process for the generation of energy and supplying the $CO_2$ generated from the burning of the methane into the algae culture. A second process is disclosed which includes the supply of CO@ to the algae culture prior to the burning of the methane to create more $CO_2$. In Paragraph [0086-87] of the Trosch patent, *Nannochloropsis oculata* is one type of algae culture mentioned as being a suitable algal culture for its process.

In two recent articles published in Internet articles, a very fast process for the extraction of crude oil from a green paste made from cultivated algae was disclosed in an article published by the pacific Northwest national Laboratory, http://pnnl.gov/news/release.aspx?id=1029, based upon a published article *Process development for hydrothermal liquification of algae feedstocks in a continuous-flow reactor*, Algae Research, Sep. 29, 2013; DOI: 10.1016/j.algal.2013: 08:005. See also, Biofuel scientists making headway on cheaper algae-based crude, Dec. 27, 2013, Collin Eaton in FuelFix at http://fuelfix.com/blog/2013/12/27/biofuel . . . . This technology is licensed by Genifuel Corporation and is working with an industrial partner to build a pilot plant using the technology. In the PNNL process, a slurry of wet algae is pumped into the front end of a chemical reactor. Once the system is up and running, out comes crude oil in less than an hour, along with water and a byproduct stream of material containing phosphorus that can be recycled to grow more algae. "With additional conventional refining, the crude algae oil is converted into aviation fuel, gasoline or diesel fuel." The waste is further processed yielding a burnable gas and substances including potassium and nitrogen, which along with the cleansed water, can be recycled to grow more algae. The biggest drawback to the present system in this article is production, the new process only processing 1.5 liters of algae per hour.

II. SUMMARY OF THE INVENTION

It is now common knowledge that certain types of algae can be converted to crude oil for use in internal combustion engines, being refines in the same manner as crude oil pumped from the earth. The chemical make-up of the extracted oils from this algae makes it a suitable substitute for combustible fuels extracted from natural crude oil production and at a much lower cost. Production of algae is a renewable and quickly accomplished in bioreactors and using processes disclosed in the prior art. However, these prior art systems and products do not accomplish the production at an accelerated rate, nor does any of the prior art use the same strain of algae under the same production conditions, using the same or similar high output production devices, nor produce the same yield as the present process. The prior art devices and methods also lack the efficient use of waste materials and other renewable and recycled components to create a near self-sustaining and ecologically friendly method for the high output production of algae and ultimately crude oil.

The primary objective of the disclosed algae growth process providing a large scale algae product which produces a great quantity of algae in an ideal controlled environment with the constituent process products provided by renewable resources, including trash, waste, and pre-treated waste water, which produce byproducts which are also useable for other purposes and also for reintroduction to the sustainable process, including growing the algae, harvesting the algae and delivering an algae product for refining the algae product, wet or dry, into a crude oil from which internal combustion engine fuels are made, including aviation fuel, gasoline, diesel fuel and burnable gasses.

III. DESCRIPTION OF THE DRAWINGS

The following drawings are submitted with this utility patent application.

FIG. 1 is a flow diagram of the disclosed process for a sustainable growth of algae in a bioreactor and for the extraction of an algae product for the conversion into biofuel product.

IV. DESCRIPTION OF THE PREFERRED EMBODIMENT

An algae growth process for the large scale production of an algae product, the process producing a large quantity of algae in an ideal controlled environment at an accelerated rate with the constituent process products provided by renewable resources, including trash, waste, and pre-treated waste water, producing byproducts which are safe for the environment, useable for other purposes and also for reintroduction to the sustainable process, the process comprising the steps of providing a waste water source 10 containing nutrients for algae culture growth and bacteria to produce methane which is further oxidized to produce $CO_2$, providing a small amount of the nutrient water which is heated to remove any live bacteria prior to introduction within a photobioreactor 20, adding a quantity of algae, and adding a large amount of pure fresh water into the photobioreactor, the photobioreactor furnishing a low cost, low wattage internal LED lighting source delivered at an optimal wavelength to stimulate the circulated algae growth, providing water borne micronutrients to feed the algae culture along with $CO_2$ to feed the algae culture and to stabilize the pH within the photobioreactor, drying the algae in two phases for a wet algae product and/or a dry powdered algae product and harvesting the wet and/or dry algae product within a harvester condenser 40 and a harvester apparatus 50 and ultimately providing a supply outlet for the wet and/or dry algae product for delivery to a processing plant to refine the algae product into a crude oil from which internal combustion engine fuels are made, including aviation fuel, gasoline, diesel fuel and burnable gasses. Recovered products from the process are reintroduced into the process to sustain the process, which include algae growth gases, cleansed water stored and collected within a fresh water storage tank 60 for return to the photobioreactor, and combustion fuels to supply the system with an amount of heat, to generate electrical power 80 and light and compel movement of the algae culture within the photobioreactor during growth. The present process does not claim the refinery of the algae product into crude oil.

The waste products from the included process include clean air, clean water, fertilizer and electricity, which makes this a completely ecologically compatible means of production of crude oil. There is no footprint, no carbon emission, no environmental contamination and no hazards associated with shipment or transportation. All the input energy is produced from waste materials which have little collateral value and are plentiful. The input products are waste water, nitrogen, trash, rubbish and debris and methane which is burned to produce carbon dioxide which is utilized by the algae to produce oxygen. The process requires little land source and does not in any way compete with food production for the process supply materials. The crude oil produced by the process is refined just like crude oil produced from drilling, except there is no environmental footprint, no clean-up, and the process is perpetual and regenerative with the production being made from renewable resources and producing renewable resource which are recycled continually within the process. It is not harmful to the environment and has no impact on groundwater or subsurface stability nor does it release greenhouse gasses or other products harmful to the atmosphere.

The first step in the process takes a contained waste water source 10 suspending nutrients and live bacteria and contains the waste water to produce methane from the active bacteria consuming the waste material within the water. This methane gas is captured and consumed later in the process for fuel heat with the burning of the methane producing carbon dioxide which is diverted as a food source and pH stabilizer for the algae culture in the photobioreactor 20. The small volume of waste water is heated to remove any live bacteria prior to introduction into the photobioreactor 20, live bacteria often inhibiting or impeding algae growth in the photobioreactor 20 under conditions suitable for the algae culture growth.

The photobioreactor 20 is unique to the process as the photobioreactor 20 involved in the process generates a large quantity of algae due to its controlled environment ideally suited for algae growth and also due to its vertical orientation, its flow generation which does not harm the algae, and its sustainability perpetuating constant algae growth since only a portion of the algae grown within the tank is harvested during the process, leaving a portion of the algae culture within the photobioreactor 20 to produce the next algae harvest crop. The photobioreactor 20 first supplies a large capacity cylindrical vertical tank made of steel, approximately 15 feet in diameter and approximately 24 feet tall. It would preferably be made of stainless steel, but to reduce costs, it can be made of a powder coated or epoxy coated steel. It will contain roughly 30,000 gallons of algae culture, which is useable volume due to the internal circulation of the algae culture with no "dead zones" or dormant areas within the photobioreactor. Outdoor algae growth tanks or flat tray culturing generally only provides a useable culture volume of 20,000 to 30,000 gallons per acre, or 20,000 to 30,000 gallons over 43,560 square feet. Using the vertical tank photobioreactor as presented in the process, the space required is approximately 200 square feet or about 0.5% of the space requirements for flat tank algae culture growth.

Within the photobioreactor 20, light is supplied through a plurality of angularly directed horizontal LED light tubes supplied by LED lights within the tube primarily within the blue and red spectrum. Sunlight can harm algae when it becomes too intense, and poor weather can limit the amount of sunlight available at any given time. High wattage lighting can burn the algae and is very costly. External lighting into a tank is inconsistent and the algae when reaching its full culture can actually block light from penetrating into the center of the culture.

The optimal light within the photobioreactor 20 is supplied by a low wattage LED bulb ratio of 3 red LEDs per blue LED. In the present process, we are preferably growing a very tiny strain of algae known as *Nannochloropsis oculata*. The LEDs are placed within water proof clear PVC tubes submerged in the center of the algae culture with the LED's arranged in a helical configuration inside the tubes as the light is projected in all directions. The light produced by the LED bulbs in the tube produce absorbed light produced by the blue LED light in the 401 to 455 nm range and absorbed light produced by the red LED lights in the 632-675 nm range, ideal for the production of algae within the photobioreactor. In pre-application testing conducted by the inventor, the amount of light optimally provided to the algae culture is not constant. Best algae culture growth was obtained by illumination of the low wattage LED lighting for 16 hours, with an 8 hour resting state with the lights off. Constant light has been found by those skilled in the art, interferes with algae reproduction, respiration and causes algae to clump as a result of stress. Apparently, just like other organisms, algae growth is best when the algae culture is giving a period of rest from illumination.

Circulation of the algae culture within the photobioreactor 20 is produced by a cylindrical draft tube which is emerged within the tank and is approximately 11 feet diameter and 20 feet tall and is suspended one inch above the floor of the tank and below the surface water level, being suspended from a tank lid. The draft tube provides a double wall with a cavity about an inch wide. The purpose for this cavity is to circulate water that is either heated or cooled to control the tank internal temperature, similar to a heat exchanger, and provides an ample surface area to control the temperature efficiently. This cavity is sealed at the top and the bottom to prevent mixing of the heating and cooling water with the algae culture, keeping them separate.

Inside the draft tube, located approximately halfway down the height of the draft tube is a bubbler or sparger. The lower surface defines a reducing tapered lower channel which is wider at the bottom than the top. A large hole is centrally positioned within the sparger creating a Venturi channel to accelerate the liquids as they move upward through the sparger. The central positioning of the sparger is essential in order for the sparger to perform its function. Placed lower within the draft tube, the gas pressure would have to be high enough to overcome the nearly 250,000 lbs. of water and algae. Too high, and the sparger would work less efficiently because the purpose of the sparger is to create a savaging effect on the circulating fluid and algae, in outer concentric circles, and also produce a chaotic turbulent flow, stirring the suspended algae culture within the water. The term savaging effect is the physical terminology for the flow of water is a stream of bubble, the water flowing in the same direction of the bubbles resulting in a convection current flow. In the present case, the water convection flow within the photobioreactor 20 is a direct result of the savaging effect, the water flow also being given a beneficial chaotic flow inside the draft tube gently mixing everything within the fluid suspension thoroughly, the chaotic flow caused by the wakes produced from multiple columns of the air bubbles through the sparger.

The strategic positioning of the sparger provides circulation to enormous volumes of algae culture at higher relative speeds, nearly 18 inches per second, without damaging the algae culture. The circulating speed can be varied from 0-18 inches per second by adjusting the gas flow rate, the gas flow rate and circulating speed directly proportional. The sparger further provides a perimeter cavity which receives gas from an external gas line through the steel tank, the perimeter cavity opening upward through a sparger top plate defining a large quantity of through and through holes in concentric circles through an upper porous surface of the sparger. Larger holes are better than small holes.

The gas bubbles emanating through the large quantity of holes propels the liquid within the photobioreactor 20 along with the suspended algae culture, to the top of the liquid level of the tank, down the outer sides of the tank, between the draft tube and the cylindrical vertical walls of the steel tank, to the bottom floor of the tank, through the approximately one inch gap between the draft tube and the tank floor, and back through the sparger repeatedly. The light tubes forming an array are placed within the draft tube above the sparger, the light tube array suspending from the tank lid through which the electrical current to the LED lights is supplied. This preferred positioning of the LED light allows the light to be inserted within the chaotic flow of the culture ensuring all the algae gets maximum illumination and also to maintain the LED light tubes within the bubble flow to keep them clean and prevent the algae from sticking to the tube outer surfaces.

A inlet water line inserts through the steel tank lid and into the cavity between the dual walls of the draft tube, as does the return outlet water line, the inlet and outlet lines provided to circulate warm or cooled water to regulate the temperature of the photobioreactor contents. A gas line which creates the bubble through the sparger provides carbon dioxide and nitrogen gas to grow and circulate the algae culture respectively. The tank also includes a water inlet line near the top of the tank supplying the culture medium with water and growth micronutrients, as needed, and a drain line located approximately half to two thirds down an opposing wall of the tank away from the inlet line. This drain line is the line through which the algae culture and water is removed when the growth of the algae culture is completed. The incomplete evacuation of the water and algae from the tank due to the positioning of the drain line leaves a portion of the algae culture within the tank at all times. All that is required for the sustained production of the algae cultures is the addition of a small amount of bacteria-free pre-treated waste water, fresh pure water and the retention of some of the algae culture within the refreshed photobioreactor.

The preferred gasses introduced into the tank comprises compressed nitrogen gas derived from a nearby nitrogen generator 25, nitrogen gas being chemically inert to algae. The aforementioned carbon dioxide gas supplied by a carbon dioxide compressor 30 is added to the photobioreactor suspension as needed to maintain the proper pH balance and growth gasses for the algae within the growth suspension which is produced as a byproduct of the combustion of the methane and recovered from other combustion gasses from the burning or oxidation of the waste within a boiler by the carbon dioxide compressor which injects the carbon dioxide gasses into the photobioreactor as needed. The ideal pH for optimal algae growth is found to be between 7.6 and 7.8. Carbon dioxide introduction is used to lower the pH of the algae culture.

After draining a portion of the algae culture from the photobioreactor 20, a wet algae product is produced. The tank is a closed system in order to sustain the algae culture growth at an optimal level, but the lid is provide with a vent filter providing a slightly positive pressure within the tank Stage one of the drying phase uses exhaust gasses from the waste water nutrient source or other means to reduce the water to algae content from approximately 93.4% water to algae to approximately 66% water to algae in the harvester condenser 40. The water removed from the culture is evacuated as captured water vapor and removed to the recycled water storage tank 60. In some instances, this first stage product may be sent for refining as a liquid slurry discussed in the articles mentioned above, whenever and if ever that technology becomes large scale.

A second stage harvester dryer 50 is further provided which takes the liquid algae slurry and sprays it on a heated inner surface of a stationary cylinder, drying the algae spray nearly on contact in a flash drying manner, wherein a rotating blade traveling being a rotating spray bar scrapes the flash dried algae off the inner wall, causing the dry algae to fall to the bottom of the stationary cylinder through a linear lower channel into an auger basin, wherein the dried algae is moved by conveyor to a container for shipping to a refinery. Vapor from the second stage harvester apparatus is condensed back into a liquid state as it is returned to the recycled fresh water storage tank 60, providing a clean water source for reuse in the system or for other clean water purpose. The steam generated by a boiler is also used to provide on-site electrical generation in an electrical steam powered generator 80 to operate the process systems requiring electricity and to provide the heat to dry the algae within the first stage harvester condenser 40 and primarily the heat used to dry the algae in the second stage harvester 50. Recycled waste products can also be employed to generate heat to produce additional steam from the fresh water byproduct of the first and second stage drying processes. It is a goal to make the process as environmentally friendly as possible and also to use a little outside energy as necessary, the system attempting to be as near to self-sustaining as traditional, modern and future science will allow.

In further pre-application testing, the inventor has found that the photobioreactor 20 is capable of producing from 100,000 algal cells per ml to over 4,500,00 algal cells per ml in 5 days, and up to 2 billion algal cells per ml in 14 days. The cycling of the algae byproduct in the bank of photobioreactors can produce a full growth algae culture every 12-24 hours per photobioreactor for an ultra high density growth concentration of algae not anticipated in any prior art.

The present process avoids issues previously demonstrated in prior art. First, there is no lack of light to the culture. It can be turned on an off and provided in the ideal light spectrum for the algae growth. Second, the process avoids any mixing within the photobioreactor 20 that can damage, impede or destroy the algae culture, such an impellers, wheels, belts or other mechanical devices, using only compressed nitrogen at a controlled and variable rate. Third, the present photobioreactor has a temperature control provided by the warm and cooled water heat exchange within the photobioreactor. This is far better than any outdoor algae production system. In fact, it would be most preferred that the present process photobioreactor may even be imbedded underground, either wholly or partially, using the earth as an insulator. Fourth, we have chosen a very small algae cell to work with—preferably the *Nannochloropsis oculata*, which is presented with cells the size of a human red blood cell, making them very fine and small at approximately 3-5 microns. In the event that the algae is difficult to harvest, prior art has demonstrated the addition of flocculates to clump the algae and make it easier to handle and remove. The fifth improvement over the prior art is the elimination of contaminants to the photobioreactor, eliminating unwanted strains of algae and live bacteria through heat treatment of the waste water nutrient source 10 prior to delivery to the photobioreactor, which would otherwise inhibit or damage the algae culture or retard its growth within the photobioreactor. Invasive, non-productive forms of algae can enter the system in open environments or non-controlled photobioreactors, similar to weeds in the garden, that deprive the good algae from the nutrients within the photobioreactor. In the event other systems experience contamination, they require a system shutdown as well as restarting their algae growth cultures. By eliminating this potential contamination, valuable production time is not lost. Sixth, the process generates some or all of the byproducts used to power and motivate the process including methane production, steam production, fresh water generation, electrical production, heat generation, and gas supply to the process.

The process for an accelerated growth of algae to produce crude oil comprises the steps of providing a waste water micronutrient source containing bacteria which produce a methane source which is burned to produce a carbon dioxide gas to feed an algae culture and methane used as a fuel in the process, introducing a small quantity of the waste water micronutrient source through a heating source to destroy any live bacteria prior to introduction into a high capacity vertical cylindrical steel photobioreactor tank, growing the algae culture within the photobioreactor having a heat exchanger within a draft tube suspended from a tank lid within the tank which provides temperature control ideally suited for the algae culture, carbon dioxide gas for the stabilization of the pH within the photobioreactor and providing essential growth gasses ideally suited for the algae culture, a sparging unit within the suspended draft tube wherein gaseous nitrogen produced by a nitrogen generator is sparged into the draft tube to create a convection flow within the photobioreactor to circulate the algae culture, and a plurality of horizontally oriented low wattage LED lights within water proof clear tubing set in a suspended array providing an ideal light spectrum suited for the algae culture, removing a portion of the algae culture and water from the photobioreactor for a first stage drying phase reducing the algae to water ratio to approximately 1:2, and packaging the algae culture and water in a slurry for delivery to a crude oil refinery for the production of diesel, aviation fuel and gasoline fro the oils extracted from the algae culture. Alternatively, the process may also comprise an intermediate step of transferring the algae culture and water to a second stage harvester and drying apparatus for complete drying into a powdered form of algae prior to packaging the dry algae for delivery to a crude oil refinery for the same biofuel production. Additional steps may include the recovery of steam to generate electricity to provide power to the process components, the recovery of $CO_2$ from the cooled exhaust gasses generated by the first stage drying phase for recycling into the photobioreactor for the pH control, the recovery of fresh water from the first and second stage drying phases for reintroduction into the photobioreactor and the further generation of steam to produce electricity heated by a furnace burning the recovered methane from the bacteria in the waste water nutrient source and other refuse, trash, garbage or rubbish, the heat from the furnace also used to provide the heat to operate both the first and second drying phases.

While the invention process has been particularly shown and described with reference to a preferred embodiment thereof, it will be understood by those skilled in the art that changes in form and detail may be made therein without departing from the spirit and scope of the invention.

What is claimed is:

1. A process for the sustainable growth of an algae culture within a controlled environment to produce algae for the extraction of a biofuel product, the process comprising the steps of:

providing a supply of waste water containing bacteria and micronutrients to produce a supply of methane;

heating a portion of said waste water to remove any live said bacteria from said waste water supply;

introducing a quantity of approximately 20 to 30 gallons of said heated waste water suitable for sustaining algae growth into at least one photobioreactor made of stainless or coated steel and defining a vertical cylinder having a lid, said photobioreactor having a volume of up to 30,000 gallons of liquid;

introducing up to 30,000 gallons of chemical-free fresh water into each at least one photobioreactor;

introducing a quantity of a selected algae culture into each at least one photobioreactor;

providing an internal light source within each at least one photobioreactor having a suitable light spectrum produced by a plurality of LED light tubes;

providing a supply of carbon dioxide through an external carbon dioxide compressor into each at least one photobioreactor to regulate the pH of each photobioreactor's contents within a suitable pH range and to provide a nutrient source for the algae culture, a portion of said carbon dioxide derived from the combustion of the methane gas byproduct;

creating a non-destructive turbulent flow within each at least one photobioreactor through a centrally suspended draft tube having an internal nitrogen gas sparger to provide a concentric current flow from a top of said tank to a bottom of said tank within each at least one photobioreactor, said nitrogen gas supplied through an external nitrogen generator;

providing a water flow within said draft tube as a heat exchanger to regulate the temperature of the contents circulating within each at least one photobioreactor;

withdrawing a quantity of the algae culture and water from each at least one photobioreactor, leaving a quantity of each photobioreactor content for regrowth upon the addition of a small quantity of said live bacteria-free waste water and said chemical-free fresh water, the withdrawn quantity of algae culture and water transferred into a harvester condenser, wherein water is vaporized through heat to reduce a water to algae ratio forming a thickened liquid algae slurry, said condensed water vapor reintroduced back into a tank wherein the chemical-free fresh water is stored and available for use within said process;

creating electricity through the use of a steam boiler, wherein the heat for the boiler is being produced by the burning of trash, rubbish and debris, with residual combustion gasses being diverted to provide the heat source for the harvester condenser, to heat said waste water to kill any active bacteria prior to introduction within each at least one photobioreactor, and to produce steam to generate electricity to operate other electrical components within the process, with said steam condensed and reintroduced back into said boiler;

transferring said liquid algae slurry to a second stage harvester dryer and then flash drying the algae slurry into a dry powdered algae product, wherein said second stage harvester dryer directs a spray of said thickened liquid slurry through a rotating spray arm onto a heated inner surface of a stationary cylinder, drying the said liquid slurry algae spray on contact in a flash drying manner, said rotating spray arm further providing a rotating blade behind said rotating spray arm which scrapes said flash dried algae off said inner wall, causing said dry algae to fall to the bottom of said stationary cylinder through a linear lower channel into an auger;

transferring the dry powdered algae product by said auger into transport containers for shipping and delivery to a crude oil refinery for rehydration and extraction of the algae oils which are further refined into aviation fuels, gasoline, diesel and other hydrocarbon fuels, the process being renewable and sustainable without using any food source for fuel, without damage to the environment and without contamination to the environment, without damage to the groundwater, the byproducts of the process being electricity, fresh water and clean air.

2. The process as disclosed within claim 1, wherein said algae is the species *Nannochloropsis oculata*.

3. The process as disclosed in claim 1, wherein each said at least one photobioreactor provides said plurality of low wattage LED light tubes illuminated by a helically wound strands of red and blue LEDs within a blue and red spectrum, each said blue LED light emitting light within a 401 to 455 nm range and each said red LED light emitting light within a 632 to 675 nm range, with said light tubes being illuminated 16 hours during each 24 hour period.

4. The process as disclosed in claim 1, wherein said pH of the contents of each said photobioreactor is between 7.6 and 7.8, with the addition of said carbon dioxide gas introduced to lower said pH of the contents when it becomes too high.

5. The process as disclosed in claim 1, wherein a water inlet is introduced through said lid upon said large capacity photobioreactor tank within a cavity defined between an inner wall and an outer wall of said draft tube with a water outlet tube further directed from said cavity within said draft tube through said lid, wherein cooled or warmed water is circulated by a pump providing said warmed and cooled water to maintain and regulate a preferred temperature of said contents of said photobioreactor tank.

6. The photobioreactor of claim 1, wherein said at least one photobioreactor having a volume of up to 30,000 gallons is approximately 15 feet in diameter and approximately 24 feet tall and occupies a ground space of approximately 200 square feet.

7. The process as disclosed in claim 1, wherein each said at least one photobioreactor provides said plurality of low wattage LED light tubes illuminated by a helically wound strands of red and blue LED lights within a blue and red spectrum, each said blue LED light emitting light within a 401 to 455 nm range and each said red LED light emitting light within a 632 to 675 nm range, with said light tubes being illuminated 16 hours during each 24 hour period, said light tubes forming an array placed within said draft tube above said sparger, said light tube array suspending from said tank lid through which an electrical current is supplied to said LED lights, said positioning of said light tube array allowing said light tube array to be inserted within a chaotic flow of said algae ensuring all said algae gets maximum illumination and also to maintain said LED light tubes within said bubble flow thereby keeping said LED light tubes clean and preventing said algae from sticking to an outer surface of said LED light tubes.

\* \* \* \* \*